US011090393B2

(12) United States Patent
Bensaci et al.

(10) Patent No.: US 11,090,393 B2
(45) Date of Patent: Aug. 17, 2021

(54) MILD SURFACTANT PREPARATION AND METHOD THEREFOR

(71) Applicant: Johnson & Johnson Consumer Inc., Skillman, NJ (US)

(72) Inventors: Jalil Bensaci, Issy-les-Moulineaux (FR); Thierry Oddos, Clamart (FR); Georgios N. Stamatas, Issy-les-Moulineaux (FR)

(73) Assignee: Johnson & Johnson Consumer Inc., Skillman, NJ (US)

( * ) Notice: Subject to any disclaimer, the term of this patent is extended or adjusted under 35 U.S.C. 154(b) by 240 days.

(21) Appl. No.: 16/220,056

(22) Filed: Dec. 14, 2018

(65) Prior Publication Data

US 2019/0209711 A1 Jul. 11, 2019

Related U.S. Application Data

(60) Provisional application No. 62/613,878, filed on Jan. 5, 2018.

(51) Int. Cl.
| | |
|---|---|
| *A61Q 17/00* | (2006.01) |
| *G06F 30/20* | (2020.01) |
| *G01J 3/44* | (2006.01) |
| *A61K 49/00* | (2006.01) |
| *A61K 8/49* | (2006.01) |
| *G01N 33/50* | (2006.01) |
| *A61K 9/70* | (2006.01) |
| *G16H 50/50* | (2018.01) |
| *G06F 16/245* | (2019.01) |
| *G01J 3/28* | (2006.01) |

(52) U.S. Cl.
CPC ........ *A61K 49/0006* (2013.01); *A61K 8/4953* (2013.01); *A61K 9/7038* (2013.01); *A61K 9/7084* (2013.01); *A61K 9/7092* (2013.01); *A61Q 17/00* (2013.01); *G01J 3/44* (2013.01); *G01N 33/5008* (2013.01); *G01N 33/5088* (2013.01); *G06F 16/245* (2019.01); *G06F 30/20* (2020.01); *G16H 50/50* (2018.01); *G01J 2003/2866* (2013.01)

(58) Field of Classification Search
CPC .. A61K 8/4953; A61K 49/0006; A61Q 17/00; G01N 33/5008; G01N 33/5088; G16H 50/50; G06F 16/245; G06F 30/20; G01J 3/44; G01J 2003/2866
See application file for complete search history.

(56) References Cited

U.S. PATENT DOCUMENTS

| | | |
|---|---|---|
| 10,036,741 B2 | 7/2018 | Mills et al. |
| 2015/0285787 A1 | 10/2015 | Msika et al. |
| 2018/0185255 A1 | 7/2018 | Wei |

FOREIGN PATENT DOCUMENTS

| | | |
|---|---|---|
| WO | WO 01/5344 A1 | 7/2001 |
| WO | WO 2015/150426 A1 | 10/2015 |
| WO | WO 2017/103195 A1 | 6/2017 |

OTHER PUBLICATIONS

Dey et al., An in vitro Skin Penetration Model for Compromised Skin: Estimating Penetration of Plyethylene Glycol [14C]-PEG-7 Phosphate, Skin Pharmacol Physiol 2015;28:12-21. (Year: 2015).*
Telofski et al., The Infant Skin Barrier: CanWe Preserve, Protect, and Enhance the Barrier? Dermatology Research and Practice vol. 2012, Article ID 198789, 18 pages. (Year: 2012).*
Waltesr et al. Designing Cleansers for the Unique Needs of Baby Skin, Cosmetics & Toiletries magazine, vol. 123, No. 12, p. 53-60. www.cosmeticsandtoiletries.com. (Year: 2008).*
Saadatmand et al. "Skin hydration analysis by experiment and computer simulations and it's implications for diapered skin", Skin Res. Technol., 2017: 1-14.
Maxwell et al. "Application of systems biology approach for skin allergy risk assessment", Proc. 6th World Congress on Alternatives & Animal use in Life Sciences. pp. 381-388 (2007).
Strube et al. "The Flex wash test: a method for evaluating the mildness of personal washing products", J. Soc. Cosmet. Chem., 40:297-36 (1989).
Keswick et al. "Comparison of exaggerated and normal use techniques for accessing the mildness of personal cleaners", J. Soc. Cosmet. Chem., 43:187-193(1992).
Frosch et al. Journal of the American Academy of Dermatology, vol. 1, Issue 1. pp. 35-41 (1979).
Paye et al. "Dansyl chloride labelling of stratum corneum: its rapid extraction from skin can predict skin irritation due to surfactants and cleansing products". Contact Dermatitis 30(2), pp. 91-96 (1994).
Sutterlin et al., "A 3D self-organizing multicellular epidermis model of barrier formation and hydration with realistic cell morphology based on EPISIM", Scientific Reports, vol. 7, article 43472, (2017).
Sutterlin et al. "Modeling multi-cellular behavior in epidermal tissue homeostasis via finite state machines in multi-agent systems", Bioinformatics, 25(16), pp. 2057-2063 (2009).
Nikolovski et al. "Barrier function and water-holding and transport properties of infant stratum corneum are different from adult and continue to develop through first year of life", Journal of Investigative Dermatology (2008), vol. 128.
Hansen et al: "In-silico model of skin 1-5 penetration based on experimentally determined input parameters. Part I: Experimental determination of partition and diffusion coefficients", European Journal of Pharmaceutics and Biopharmaceutics, Els ev i er Sci ence Publishers B. V Amsterdam, NL, vol. 68, No. 2, Jan. 10, 2008 (Jan. 10, 2008), pp. 352-367, XP022415429, ISSN: 0939-6411, DOI: 10.1016/J.EJPB.2007.05.012 abstract sections 2.9, 2.10, 2 .11 t 2 .14.
Thomas S0tterlin et al: "A 3D self-organizing multicellular epidermis model of barrier formation and hydration with realistic cell morphology based on EPISIM", A A Scientific Reports, vol. 7, No. 1, Mar. 6, 2017 (Mar. 6, 2017), XP55578035, . DOI: 10.1038/srep43472 the whole document in particular Figure 2.
Robert J 0 'Connor et al: Induction of epidermal damage by tape stripping to evaluate skin mildness of cleansing regimens for the premature epidermal barrier11, International Journal of Dermatology, vol. 55 (Suppl. 1), Jul. 2016 (Jul. 2016), pp. 21-27, XP55578104, the whole document.

(Continued)

*Primary Examiner* — Robert A Wax
*Assistant Examiner* — Nabila G Ebrahim
(74) *Attorney, Agent, or Firm* — Laura A. Donnelly

(57) ABSTRACT

A method of selecting a surfactant system suitable for infants and young children is disclosed.

8 Claims, 13 Drawing Sheets

(56) References Cited

OTHER PUBLICATIONS

Mark D. A. Van Logtestijn et al: "Resistance to Water Diffusion in the Stratum Corneum Is Depth-Dependent", PLOS ONE, vol. 10, No. 2, Feb. 11, 2015 (Feb. 11, 2015), p. e0117292, XP055578012, DOI: 10.1371/journal.pone.0117292 abstract p. 2/12, paragraph 3-5 p. 3/12, paragraph 1—p. 5/12, paragraph 3 p. 6/12, paragraph 2—p. 7/12, paragraph 5.
Visscher Marty et al: "Emollient Therapy for Newborn Infants—A Global Perspec", Newborn and Infant Nursing Reviews, W.B. Saunders, Amsterdam, NL, vol. 14, No. 4, Oct. 24, 2014 (Oct. 24, 2014), pp. 153-159, XP029115610, ISSN: 1527-3369, DOI: 10.1053/J.NAINR.2014.10.003 abstract p. 154, column 2, paragraph 3—p. 155, column 2, paragraph 3.
International Search Report for PCT/IB2018/060128 dated Apr. 23, 2019.
International Search Report for PCT/IB2018/060130 dated Apr. 23, 2019.

\* cited by examiner

MILD SURFACTANT PREPARATION AND METHOD THEREFOR

This application claims priority of the benefits of the filing of U.S. Provisional Application Ser. No. 62/613,878, filed Jan. 5, 2018, the contents of which are hereby incorporated by reference herein in their entirety.

FIELD

The present invention relates to the development of mild surfactant systems, particularly for infants or young children, while assessing the level of skin irritation through analyses of adult skin tests. The invention allows one to evaluate the irritation level of a surfactant system with objective data while avoiding the need to test on young children or infants.

BACKGROUND

Skin cleansers contain surfactants, which may compromise the integrity of skin barrier to the penetration of external aggressors, resulting in skin irritation. Assessing cleanser mildness on skin is typically done by clinical evaluation and measurement of alterations in trans epidermal water loss (TEWL) following exaggerated patch test or exaggerated wash test protocols. These methods are partly subjective and often with variable results.

Skin care product mildness (particularly for cleansing products that contain potentially irritating surfactant systems) is typically assessed in vivo in adults using normal-use tests, exaggerated (repeated) use tests or patch tests. Even for baby products, the assessment is first done in adults and once passed it is sometimes followed with normal-use tests in infants. Mildness is evaluated as lack of irritation (typically skin erythema (redness)). The effects on the skin barrier are typically assessed instrumentally by measurements of Trans-Epidermal-Water-Loss (TEWL). The effects of products on the skin barrier may also be studied ex vivo using Franz cells and measuring skin impedance.

However, the previous methods suffer from a number of defects and concerns. For example, normal use tests typically require large panel sizes in order to differentiate between varying levels of mildness, which can become expensive and time-consuming. In patch tests, the surfactants can respond differently under occluded versus normal use conditions. The results of arm immersion tests can be weather-dependent. In flex wash tests, the tested skin site may not be representative of other areas of the body.

Further, each of the above items is evaluated subjectively (clinical observation), which may introduce variabilities. Finally, the majority of these tests are either geared toward adult skin without adequate correlation to infant skin, or these studies are performed on infants/young children, and clinical studies on infants raises ethical and technical questions. As noted, the validity of directly transferring data acquired on adults to the case of infant skin has been questioned. For example, infant skin is not typically used in Franz cells and the transfer of these data to infant skin is questionable. These methods are used always involving a margin of safety factor (typically 10 times) that reflects the uncertainty.

It would be useful to develop a method that can evaluate the impact of a surfactant system on infant and/or young child skin barrier by objectively assessing the concentration profile of a marker (such as caffeine) that penetrated into the skin of adult subjects. The present invention seeks to evaluate the impact through the use of biomarker testing on adult skin, using a computational model to evaluate the impact on infant/young skin, and developing a surfactant system as a result of these tests and analyses.

Moisturizers are mixtures of chemical agents specially designed to make the external layers of the skin or hair softer. Personal care compositions having moisturizing properties are known. Consumers expect such compositions to satisfy a range of requirements. Apart from the skin/hair-care effects which determine the intended application, value is placed on such diverse parameters as dermatological compatibility, appearance, sensory impression, stability in storage and ease of use. Another benefit provided by many moisturizers is protection of the skin from exposure to external environment and agents.

DETAILED DESCRIPTION

Figure 1A:
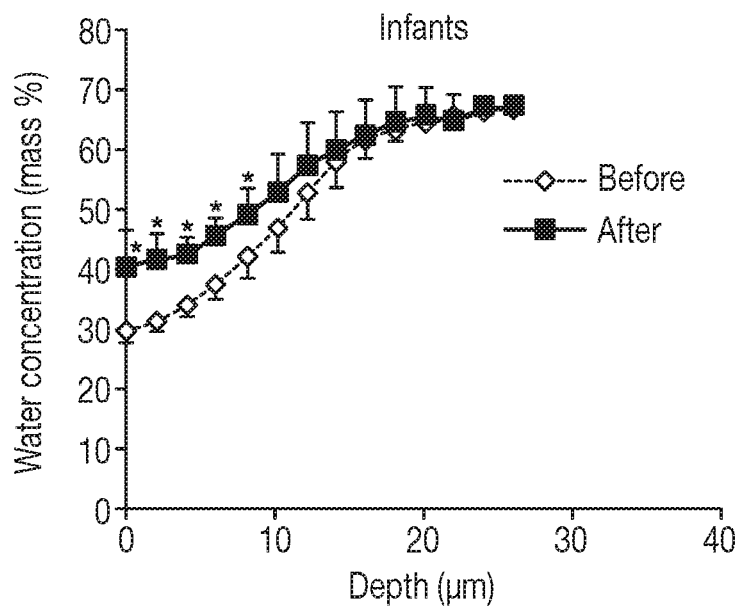
FIGS. 1A and 1B show the observation of the absorption of exogenously applied water via Raman confocal microspectroscopy 10 seconds after water application to the skin of the lower ventral arm.
Figure 1B:
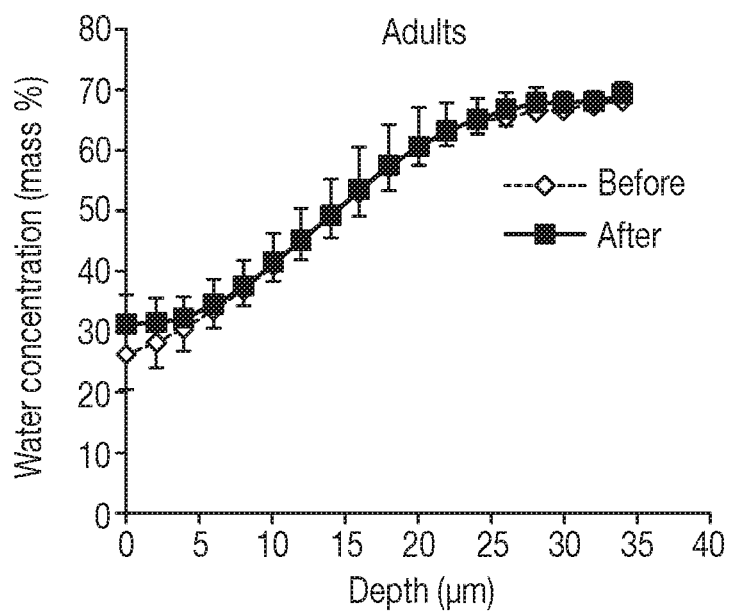

The present invention relates to a process for assessing the mildness of a skin care product on infant skin and specifically the effect of topical application of a substance and/or formulation on the skin barrier of infants, and preparing and/or using a surfactant system based upon this evaluation. As used herein, the term "infant skin" refers to skin of newborn human children, but also refers to and includes skin of children that are up to 12 months old. The term "young child" or young children" refers to infants but also includes children that are 12 to 36 months old.

The purpose of the present invention is to be able to assess product safety, mildness, etc. on the skin of infants and/or young children by safely evaluating the product on adult skin. The process involves applying the substance on adult skin, collecting penetration data of a marker on the treated adult skin, transferring the information to a computational model of adult skin, extracting penetration parameters from this model, transferring the parameters to a computational model of infant skin and visualizing the penetration of the marker in infant skin model and drawing conclusions about the effects of the topical product on the infant skin. Ultimately the process then includes preparing a surfactant system as a result of this evaluation, and/or using a surfactant system based upon this evaluation and ultimate preparation of the system.

U.S. Published Application No. 20150285787 to Laboratoires Expanscience discloses a method for identifying at least one biological marker of children's skin that comprises: a) measuring the level of expression of a candidate biological marker in at least one sample of skin cells (A), said sample being obtained from a donor under 16 years of age, b) measuring the level of expression of said candidate biological marker in at least one control sample (B) of skin cells, c) calculating the ratio between the level of expression of step a) and the level of expression of step b), and d) determining whether the candidate marker is a biological marker of children's skin.

WO2015150426 and WO2017103195 to Laboratoires Expanscience disclose methods of evaluating in vivo formulations that comprise a) contacting an active agent or a formulation with a reconstructed skin model, said model being obtained from a skin sample from a child; b) contacting the reconstructed skin model after step a) with urine; and c) measuring the expression level of at least one of a list of specified biological markers in the skin model after step b.

U.S. Published Application No. 20180185255 to Procter & Gamble discloses a method of screening cleansers for mildness, comprising: a) measuring the level of one or more ceramides on an area of skin prior to application of a cleanser; b) applying the cleanser to the area of skin for at least 7 days; c) measuring the level of one or more ceramides after the product application of at least 7 days on the area of skin; wherein the cleanser is mild if the level of the one or more ceramides is at least 10% vs. the no treatment control.

U.S. Pat. No. 10,036,741 to Procter & Gamble discloses a method for evaluating the influence of a perturbagen on skin homeostasis and formulating a skin care composition comprising the perturbagen that comprises causing a computer processor to query a data architecture of stored skin instances associated with a perturbagen with an unhealthy skin gene expression signature, wherein the query comprises comparing the unhealthy skin gene expression signature to each stored skin instance and assigning a connectivity score to each instance.

EP 1248830A1 to Procter & Gamble discloses the use of a forearm controlled application test to assess surfactant mildness.

Saadatmand et al., Skin hydration analysis by experiment and computer simulations and its implications for diapered skin, Skin Res. Technol., 2017: 1-14, discloses a stratum corneum reversible hydration model that simulates evaporative water loss and stratum corneum thickness as a function of exposure scenarios such as time-dependent relative humidity, air temperature, skin temperature and wind velocity.

Maxwell et al., Application of a systems biology approach for skin allergy risk assessment, Proc. $6^{th}$ World Congress on Alternatives & Animal Use in Life Sciences, pp. 381-388 (2007) discloses an in silico model of skin sensitization induction to characterize and quantify the contribution of each pathway to the overall biological process.

Strube et al., The flex wash test: a method for evaluating the mildness of personal washing products, J. Soc. Cosmet. Chem., 40:297-306 (1989), discloses the use of a sixty second wash, three times daily, of the flex arm to assess potential irrancy of washing products.

Keswick et al., Comparison of exaggerated and normal use techniques for accessing the mildness of personal cleansers, J. Soc. Cosmet. Chem., 43:187-193 (1992), discloses the comparison of the forearm test and flex wash test to home use to determine how well the tests approximate ad lib usage.

Frosch et al., Journal of the American Academy of Dermatology, Volume 1, Issue 1, 35-41 (1979), discloses a chamber test to assess the irritancy of soaps that entails five weekday exposures to 8% solutions with readings of scaling and redness.

Many in vivo tests are not acceptable for experimental use on infant skin. The cited references do not disclose or suggest the evaluation of adult skin and the use of computational models to correlate how an ingredient would affect infant skin. The invention thus avoids the need to conduct an in vivo test on infant skin.

Unless defined otherwise, all technical and scientific terms used herein have the same meaning as commonly understood by one of ordinary skill in the art to which the invention belongs. Also, all publications, patent applications, patents, and other references mentioned herein are incorporated by reference in their entirety herein. As used herein, all percentages are by weight unless otherwise specified. In addition, all ranges set forth herein are meant to include any combinations of values between the two endpoints, inclusively.

In the present invention, the method can be used to discriminate between different cleanser formulations according to their effect on skin barrier to external penetration. The present invention sets forth a method of analyzing the formulation that objectively evaluates the effects of topical cleansers on skin barrier to the penetration of external aggressors and can be used to assess cleanser mildness. One can take the results of this analysis and provide or prepare a suitable formulation that is considered mild to an infant's and/or a young person's skin.

The present invention is drawn to a predictive method for assessing the mildness of a topical substance toward the skin of a subject, preferably young infant. It also relates to a predictive method to assess the penetration of a compound (marker) through the skin of infants. The present invention also relates to a predictive method for assessing the influence of a topically applied substance on the penetration of a compound (marker) though infant skin. In addition, the present invention may provide a method to measure and/or predict the effect of barrier enhancement of topical substance(s).

In one aspect, the present invention may include a number of process steps. It may include a Phase 1 (in vivo) and Phase 2 (in silico), with optional Phase 3 (intellectual process) and finally the process concludes with the preparation of a suitable surfactant system that has been analyzed to pass the aforementioned tests, or the process concludes with the application of a surfactant system onto the skin of an infant and/or young child.

Phase I, In Vivo
  A. Applying a topical substance on adult skin, such as through direct application or application on a patch or other delivery system.
  B. Topically apply a marker on the adult skin and collect penetration data of said marker on the substance treated adult skin. This step includes applying the marker and then following its concentration profile through the skin for example using confocal Raman micro-spectroscopy (CRM).

Phase II, In Silico
  C. Transferring the information (penetration data) to a computational model of adult skin and extracting penetration parameters from this model.

This step can also be described as using a computational adult skin penetration model to visualize the penetration of the marker by optimizing the penetration parameters (for example local surface concentration and permeability coefficients) so that the model penetration profiles will match the experimental data.

D. Transferring the penetration parameters (following appropriate transformations) to a computational model of infant skin and visualizing the penetration of the marker in infant skin model.

(Optional), Phase III, Intellectual Process

E. Drawing conclusions about the mildness (effects) of the topical product on the infant skin, based on the amount of marker that has penetrated the baby skin model.

Once the aforementioned process steps have been completed and the conclusions in Step E are made, the surfactant system may be prepared, applied, or distributed by the user.

Topical Substance

The invention includes one or more topical substances to be evaluated, where the topical substance is desired to be used in the final surfactant system. The topical substance is any type of substance applied on the skin that has an effect on the permeability of the stratum corneum. The topical substance will modify the permeation of the marker through the skin. By measuring the marker permeation, the effect of the topical substance may be assessed. Typically, for the test outlined above, the topical substance is impregnated on a patch that is held in contact with the skin for 30 minutes before the marker is applied. The patch may include one or more topical substances for application testing.

Different types of topical substance can be evaluated in the scope of the present invention, for example, the topical substance may be a harsh substance(s) that can decrease the barrier properties of the skin and increase the permeation of the marker. In this case the present invention can allow one to create a mildness classification of the substance(s) and help to opt for a milder solution when designing a new skin product composition, without in vivo or in vitro testing. In other aspects, the topical substance may include a barrier substance(s), that are designed to help protect the skin and increase its barrier property, thus reducing the permeation of marker though the skin. As noted above, the present invention can help to select the most efficient solution without having to perform in vitro or in vivo testing on infant skin.

Marker

The present invention uses one or more markers or biomarkers in the evaluation method. Any type of marker is suitable, as long as there is a method to trace the marker and generate a concentration profile (e.g., penetration data). In the example of using confocal Raman micro-spectrometry, the marker should have a traceable signal in the Raman spectrum. In another example a fluorescent marker can be traced using confocal fluorescence microscopy. The penetration kinetics of the marker ideally should be such that a steady state of concentration profile is reached within reasonable time (for example in up to one hour).

The marker can be hydrophilic, lipophilic or amphoteric which will define what type of barrier effect the evaluator is examining. For example, one suitable marker is caffeine. In the case of caffeine the analysis examines the barrier to hydrophilic substances.

A marker according to the present invention may include any molecule that is safe toxicologically and dermatologically, has reasonable penetration kinetics and is traceable by confocal analysis.

Safety; some markers used in the past are not acceptable due to toxicity reasons (Dansyl Chloride (proposed in Paye et al. "*Dansyl chloride labelling of stratum corneum: its rapid extraction from skin can predict skin irritation due to surfactants and cleansing products*" Contact Dermatitis 30(2), 91-96, 1994) has been discontinued due to risk of sensitization and skin corrosion upon skin contact).

Penetration kinetics; a molecule that penetrates the skin, e.g., is fast enough but not too fast. E.g., a molecule that has a permeability coefficient close to caffeine may be employed: $kp = 1.16 \times 10^4$ cm/h reported in Dias M et al. "*Topical delivery of caffeine from some commercial formulations*" Int J Pharm 1999182(1): 41-7

Confocal analyses are noninvasive and provide data about depth penetration of markers. In contrast, for example, tape stripping is invasive and destroys the barrier; this is not acceptable in the present invention.

Penetration Data

The present invention analyzes penetration data. Penetration data is a concentration profile; this means the concentration of the marker as a function of depth through the skin. The present invention may use any desired analytical method suitable to measure the concentration profile of a marker as a function of depth in the skin and more precisely in the epidermis and particularly the Stratum Corneum. Any desired methods may be used, while non-invasive methods are preferred. Confocal techniques are preferred because they are noninvasive and provide reasonable resolution, for example 3 to 5 μm resolution in the perpendicular to skin surface direction, up to 200 μm in depth. One such method includes confocal Raman micro-spectrometry, but other methods, including confocal fluorescence microscopy, may be used.

Computational Model of Adult/Infant Skins

The present invention uses computational models to evaluate the components of the surfactant system tested. Any model that can result in a concentration profile of a marker through skin may be employed. The user may choose any type of computational skin penetration model that, given the penetration parameters, can result in a concentration profile of a marker through the skin. The use of both adult skin and skin models requires that the models take into account the structure of the skin architecture and the differences there exist between the two.

For example, one can use the physiological model published in Sutterlin et al., "A 3D self-organizing multicellular epidermis model of barrier formation and hydration with realistic cell morphology based on EPISIM", Scientific Reports, volume 7, article 43472, 2017; with modification to integrate substances (e.g., the marker) diffusion though the skin layers.

Sutterlin et al. discloses a cell behavioural model (CBM) encompassing regulatory feedback loops between the epidermal barrier, water loss to the environment, and water and calcium flow within the tissue. The EPISIM platform consists of two ready-to-use software tools: (i) EPISIM Modellar (graphical modelling system) and (ii) EPISIM Simulator (agent-based simulation environment). Each EPISIM-based model is composed of at least a cell behavioural and a biomechanical model (CBM and BM). The BM covers all spatial and biophysical cell properties. CBMs are models of cellular decisions. A 2D or 3D version of the model may be used in accordance with the invention (a version of the 2D model, but without the stratum corneum component, is described in: Suetterlin et al. "Modeling multi-cellular behavior in epidermal tissue homeostasis via finite state machines in multi-agent systems", Bioinformatics, 25(16), 2057-2063, 2009.

In one method, the process begins by the user letting the simulation reach a steady state corresponding to epidermal homeostasis. Then, at a given timepoint corresponding to the topical application of the marker, the evaluator introduces a user-defined variable corresponding to the skin surface concentration ($C_{surface}$) of the marker. The value of this parameter is defined from the concentration profile obtained experimentally and corresponds to the marker concentration at depth 0 (skin surface). A cell variable is introduced to the model defining the concentration of the marker in the cell ($C_{cell}$). At each time this parameter is modified based on the Fick's law of diffusion, as the marker is allowed to diffuse from each cell to its immediate neighbors. To apply Fick's law, a permeability coefficient parameter (P) is introduced in the model. This permeability coefficient parameter inherently accounts for the diffusion coefficient, the resistance to diffusion due to a partition coefficient and the resistance to diffusion due to the distance of the path that the substance has to cross to go from one cell to the next. The permeability coefficient is different for the stratum corneum ($P_{SC}$) compared to the viable epidermis ($P_{VE}$). If the substance reaches the lowest part of the epidermis, it is allowed to diffuse to the dermal compartment which is modeled as a penetration "sink".

These modifications apply both to the adult skin and the infant skin model.

The infant skin model is created by modifying the parameters of the adult model to reflect the higher turnover rate (proliferation and desquamation) in baby skin.

Then, the marker penetration is allowed to reach steady state at the infant skin model (about 1000 steps with each step corresponding to 30 min physiology time). At steady state, the average concentration profile of the marker is calculated (average concentration as a function of depth). The area under the curve (AUC, integral) is calculated for the concentration profile down to a defined depth (such as 20 μm).

A mildness index scale can be defined from the AUC values corresponding to different product treatments. This is an arbitrary scale used to classify the mildness of the topical substances.

This mildness index value allows the evaluator to compare the mildness of the tested topical substance with respect to two reference substances; water (mild) and sodium lauryl sulfate (SLS) 0.1% (harsh). With water and SLS 0.1% as the two reference points it is possible to build a scale to measure mildness of other topical substances.

It should be noted that this mildness indicator is optional, and one can omit the mildness indicator and directly compare the relative mildness of different topical substances directly to one another based on the integration of their predictive penetration curves (i.e., the calculated AUC values).

EXAMPLES

Figure 2:
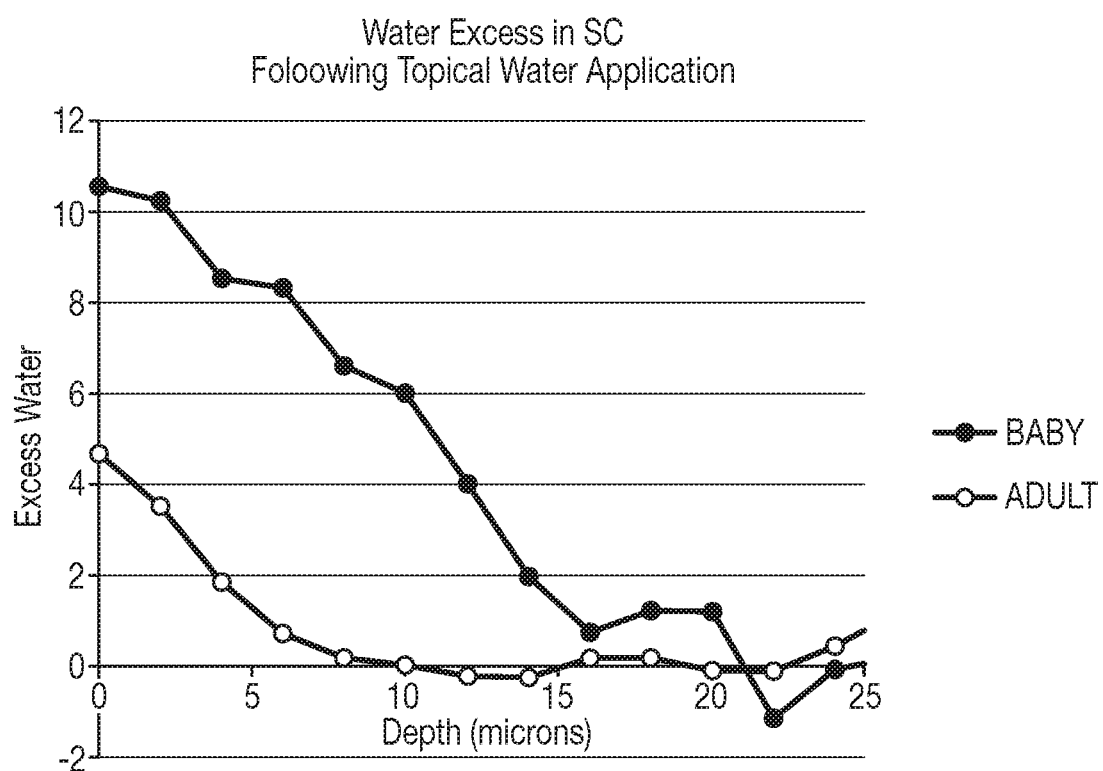
FIG. 2 shows a comparison between experiment (adult), model (adult) and prediction (baby).

1—Comparison Between Experiment (Adult), Model (Adult) and Prediction (Baby). See FIG. 2.
Goals:
  Show the predictive effect on infant skin of two extreme topical solutions, one harsh (containing 0.1% SLS), and one mild (water).
  Show that the adult model fits with the experimental data.
  Show that topical substances don't have the same effect on adult and infant skin, infant skin being more permeable to marker.

Figure 3:
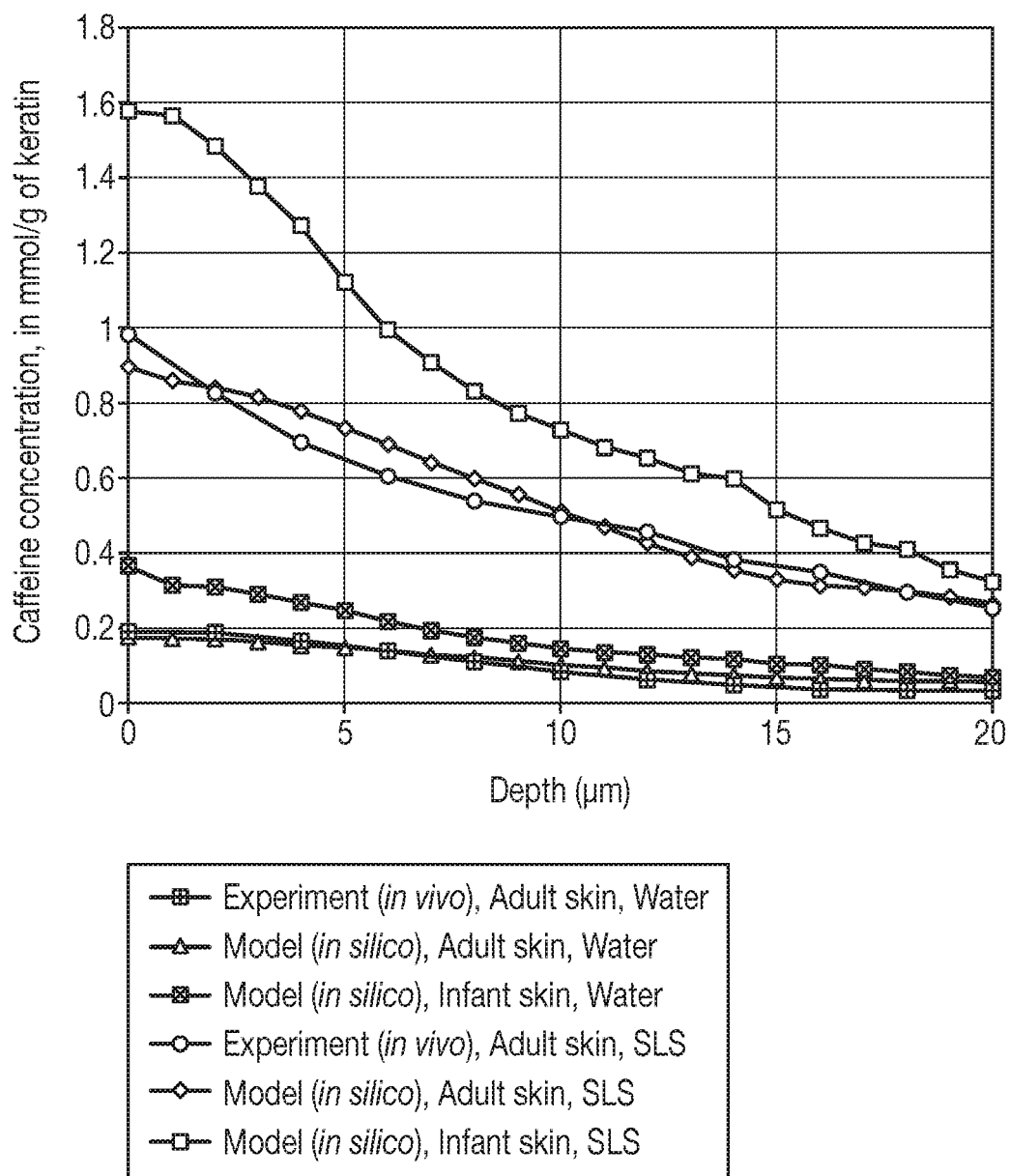
FIG. 3 shows a comparison between experiment, model and prediction for Water and SLS, on adult and infant skin.

Comparision Between Experiment, Model and Prediction for Water and SLS, on Adult and Infant Skin. See. FIG. 3.

FIG. 3 above shows the depth (in μm) of penetration of caffeine (marker) expressed in mmol per gram of keratin, obtained by in vivo experiment on adult skin (lines + and ○) or in silico predictive model (lines Δ, x, ◇ and □).

The effect of 2 topical solutions on caffeine penetration is displayed in Graph 1: water and 0.1% SLS. Model calculated data for adult are represented by lines Δ and ◇; for water and SLS respectively. Predictive data for infant are represented by lines x and □, for water and SLS respectively.

In vivo experimental data is collected on adult skin then transferred in an adult skin model to simulate the caffeine depth of penetration in an adult skin. Prediction of the penetration of caffeine in the infant skin proposed by the present invention model is represented in diagonal cross line (x) when the skin is treated with a water patch prior to caffeine application and by a square line (□) when the skin is treated with a 0.1% SLS patch prior to caffeine application.

Area under the curve from 0 to 20 μm of skin depth gives an indication of the level of mildness of the topical substance. The lower the milder to the skin. The area under the curve is a key parameter to be able to compare different treatment.

Figure 4:
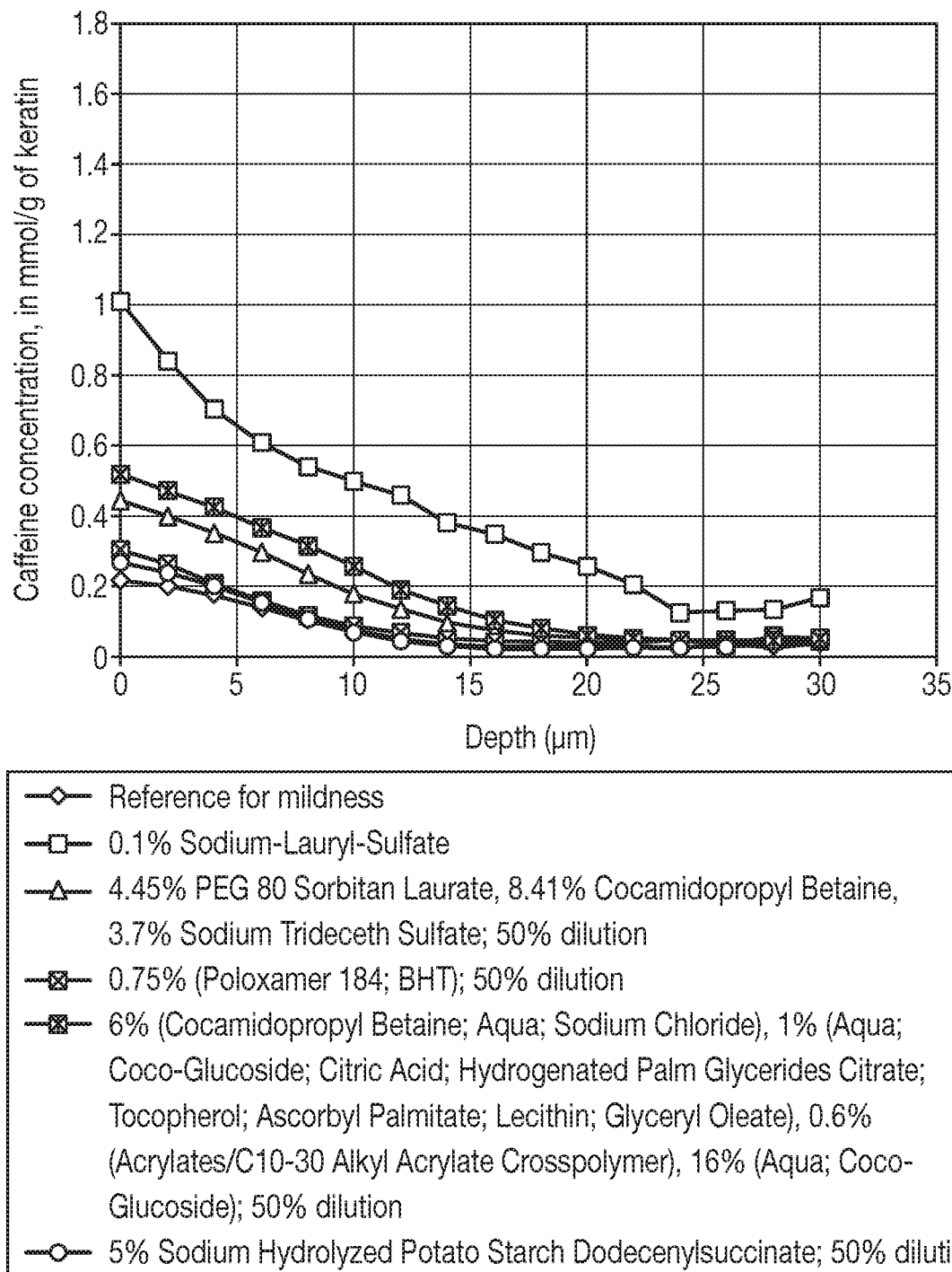
FIG. 4 shows a comparison between several surfactant formulations.
Figure 5:
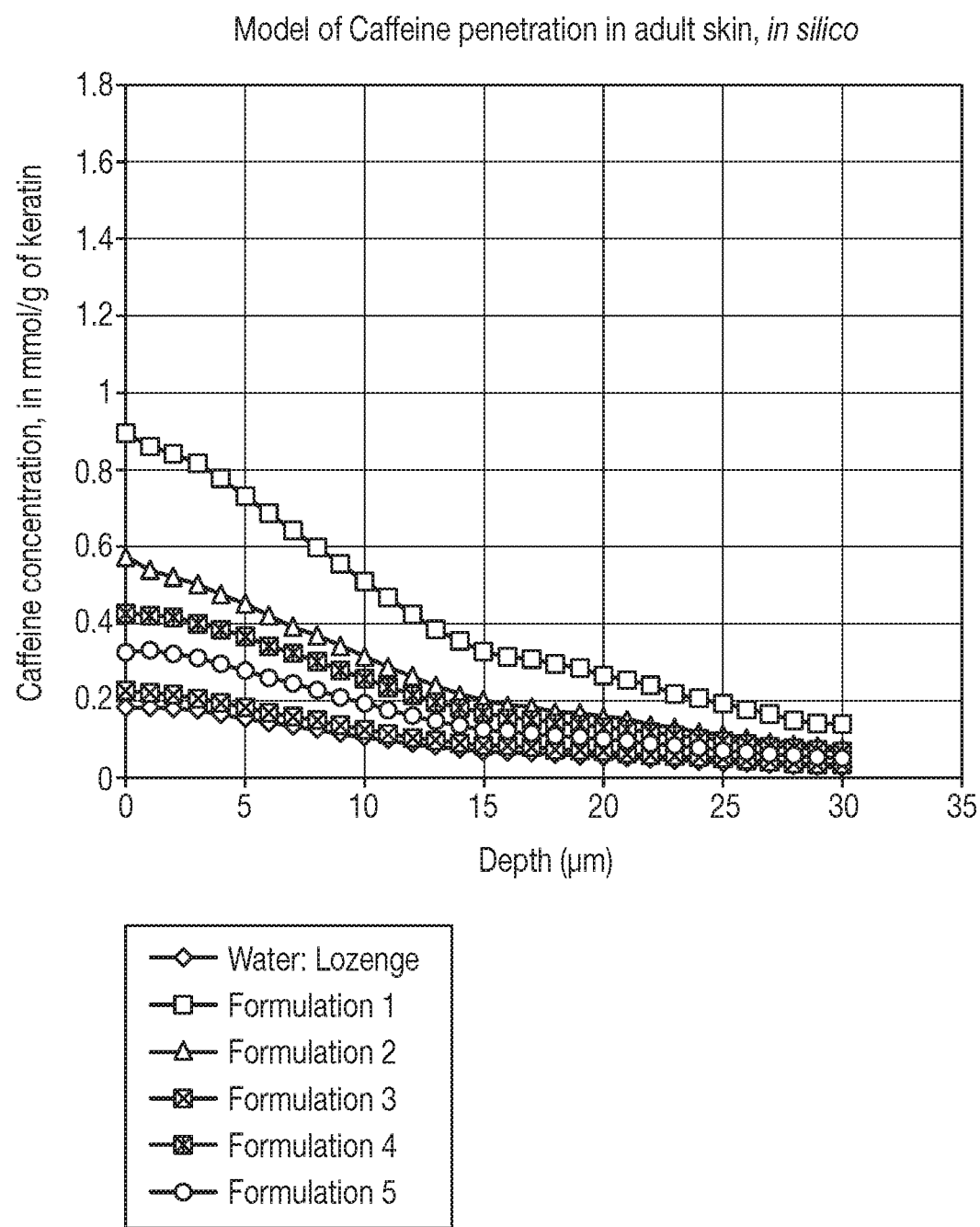
FIG. 5 shows modeling experimental data in the Adult epidermal model, in silico.
Figure 6:
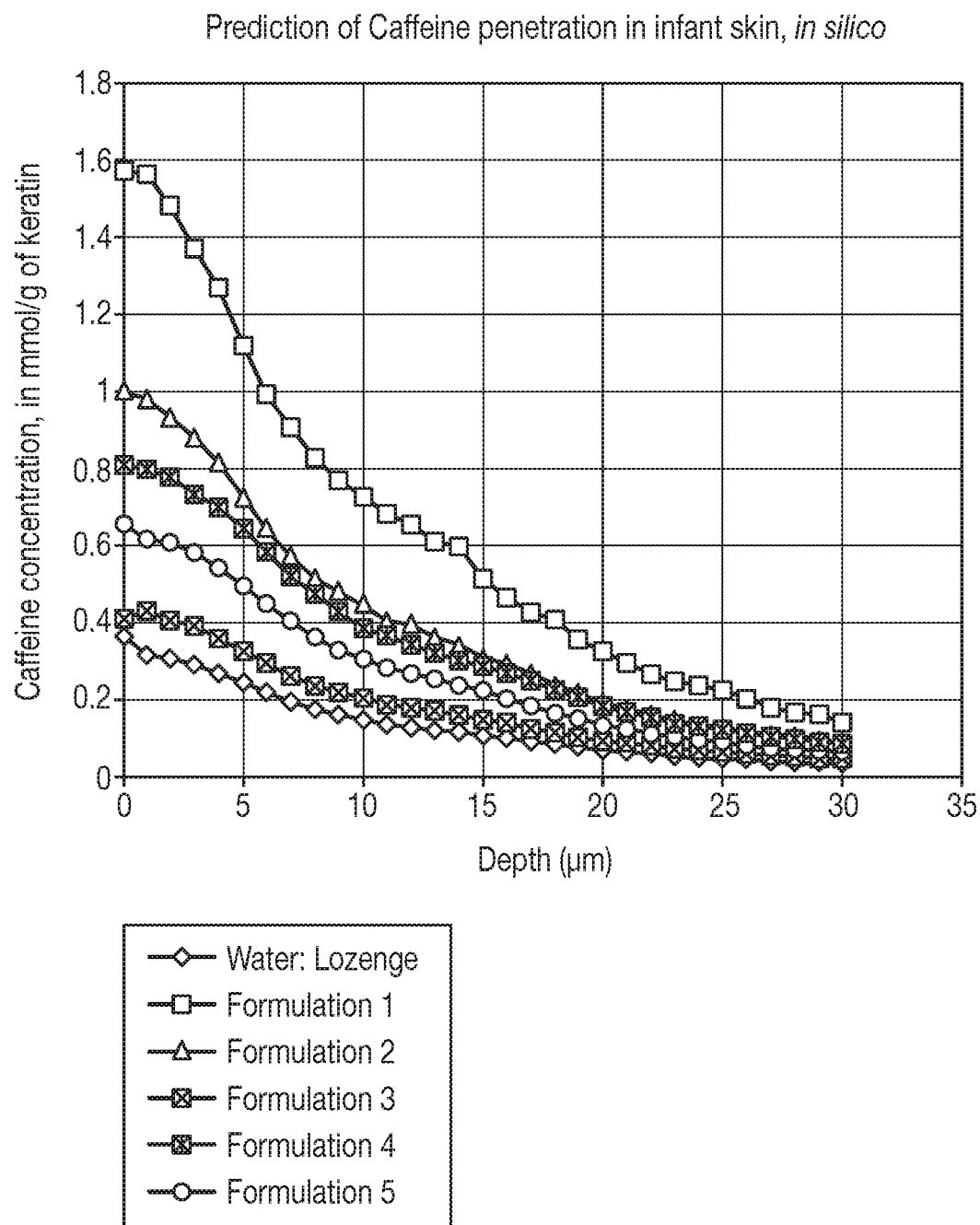
FIG. 6 shows predictive caffeine permeation curves following surfactant treatment.
Figure 7:
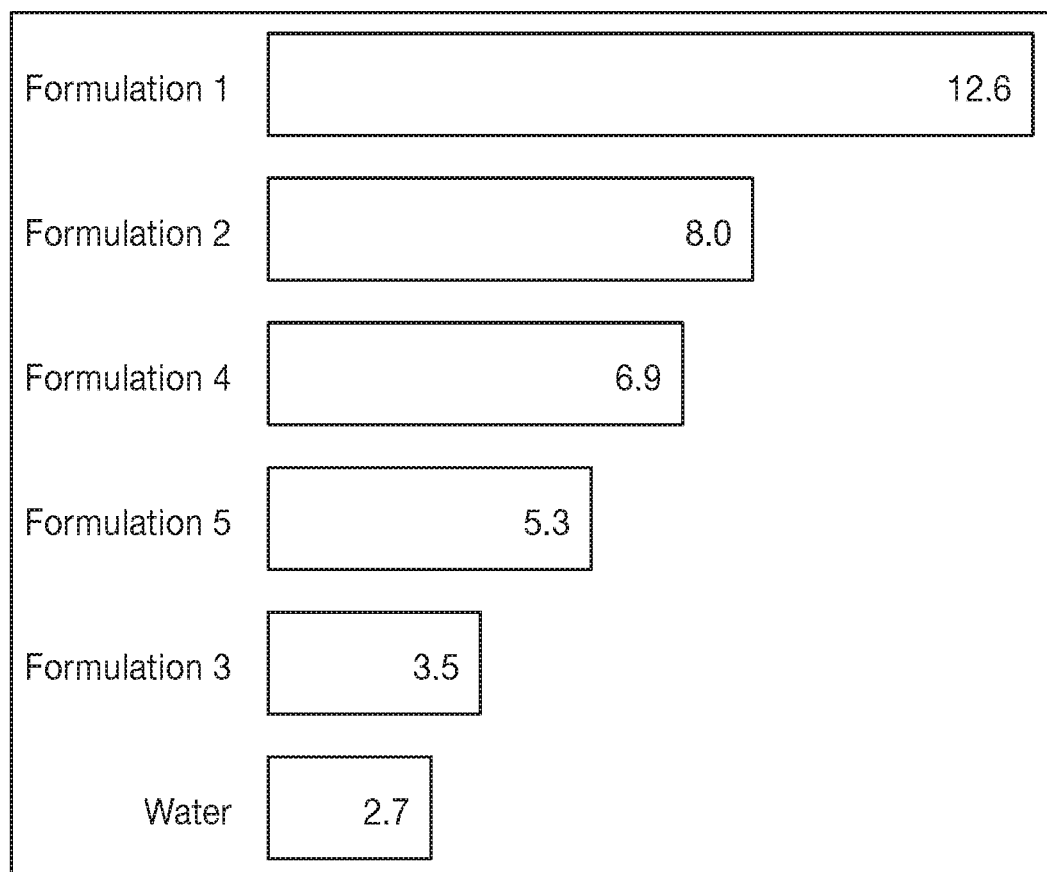
FIG. 7 shows predictive absorbed amount in baby Stratum Corneum, Area under the Curve for 0-10 μm of depth (mmol caffeine/g keratin).

2—Comparison Between Several Surfactant Formulations. See FIG. 4.
Goal:
  Create a predictive surfactant formulation classification based on their mildness to infant skin.
Step 2.1: Experimental Data, Caffeine Penetration in Adult Skin, In Vivo
  Formulations Tested are shown in FIG. 4
  Experimental protocol is as disclosed in the material and method of article Stamatas et al., Development of a non-invasive optical method for assessment of skin barrier to external penetration, Biomedical Optics and 3D Imaging OSA (2012). Stamatas et al. discloses the use of characteristic Raman spectrum of caffeine to track caffeine penetration through adult skin to demonstrate the impact of (1) sodium lauryl sulfate and (2) barrier cream on stratum corneum barrier function.
Step 2.2: Modeling Experimental Data in the Adult Epidermal Model, in Silico. See FIG. 5.
  Experimental caffeine penetration data collected at step 2.1 are transferred to a computational model of adult skin. Simulation of skin penetration is performed for each topical substance; a single simulation per substance may be sufficient. Caffeine penetration parameters (local surface concentration and permeability coefficients) are extracted.
Step 2.3: Predictive Caffeine Permeation Curves Following Surfactant Treatment. See FIG 6.
  Caffeine penetration parameters obtained from the adult skin model at steps 2.2 are transferred to a computational model of infant skin. Simulation of infant skin penetration is performed for each topical substance. Predictive caffeine penetration results are extracted and displayed in Graph 4 above.
Step 2.4: Predictive Absorbed Amount in Baby Stratum Corneum, Area Under the Curve for 0-10 Um of Depth (Mmol Caffeine/g Keratin). See FIG. 7.
  Predictive curves for each topical agent displayed in graph 4 in step 2.3 are integrated to obtain, for each topical agent, a predictive amount of the caffeine absorbed in the infant stratum corneum. These values are displayed in In FIG. 7.

In other words, this predictive graph shows how much caffeine will penetrate within the first 10 μm (not mm) of SC. The more caffeine we have, the more aggressive is the topical substance.

Results

Surprisingly, it can be predicted from this graph that the topical agent will not have a mildness index value regarding infant skin always reflected by the experimental values obtained on adult skin:

Formulation 3 will be milder than Formulation 5.
Formulation 4 will be milder than Formulation 2.

As a result of this experiment, a composition including the formulation in Formulations 3 and/or 4 can be prepared and applied to the skin of infant and/or young skin as preferable to Formulations 5 and 2 correspondingly.

In the next embodiment, the invention relates to the development of barrier systems, particularly for infants or young children, while assessing the level of barrier effect through analyses of adult skin tests.

The invention allows one to evaluate the protection level of a barrier system with objective data while avoiding the need to test on young children or infants.

Method

Steps I and II disclosed above remain the same. Predictive data on infant skin penetration of a marker are generated.

Step III differs in that the data relates to use of low penetration and diffusion of the marker through the skin to predict the barrier effect that the topical substance applied in step I A would have on an infant or baby skin.

Leave-on products (e.g., creams/moisturizers) may be assessed using this methodology Experiments Example 3

Material & Method

Data on adult skin were collected on healthy volunteers, with normal skin, who agreed not to use any other skincare treatment on the forearms for at least 24 hrs before the study and during the study.

Instrument Used:
In vivo Confocal Raman Microspectrometer (Skin Composition Analyzer Model 3510, River Diagnostics, Rotterdam, The Netherlands)

Caffeine patch: 180 mg of Caffeine in 10 mL of demineralized water, 1.8%

Example 4 Barrier Cream Simulation

Experimental data were collected on 5 female volunteers, aged between 20 and 35 years.

Topical substance tested:
Barrier cream: Desitin® Creamy (diaper rash cream)
US INCI list: Zinc oxide 10%, inactive ingredients (aloe barbadensis leaf juice), cyclomethicone, dimethicone, fragrance, methylparaben, microcrystalline wax, mineral oil, propylparaben, purified water, sodium borate, sorbitan sesuileate, vitamin E, white petrolatum, white wax.

Figure 8:
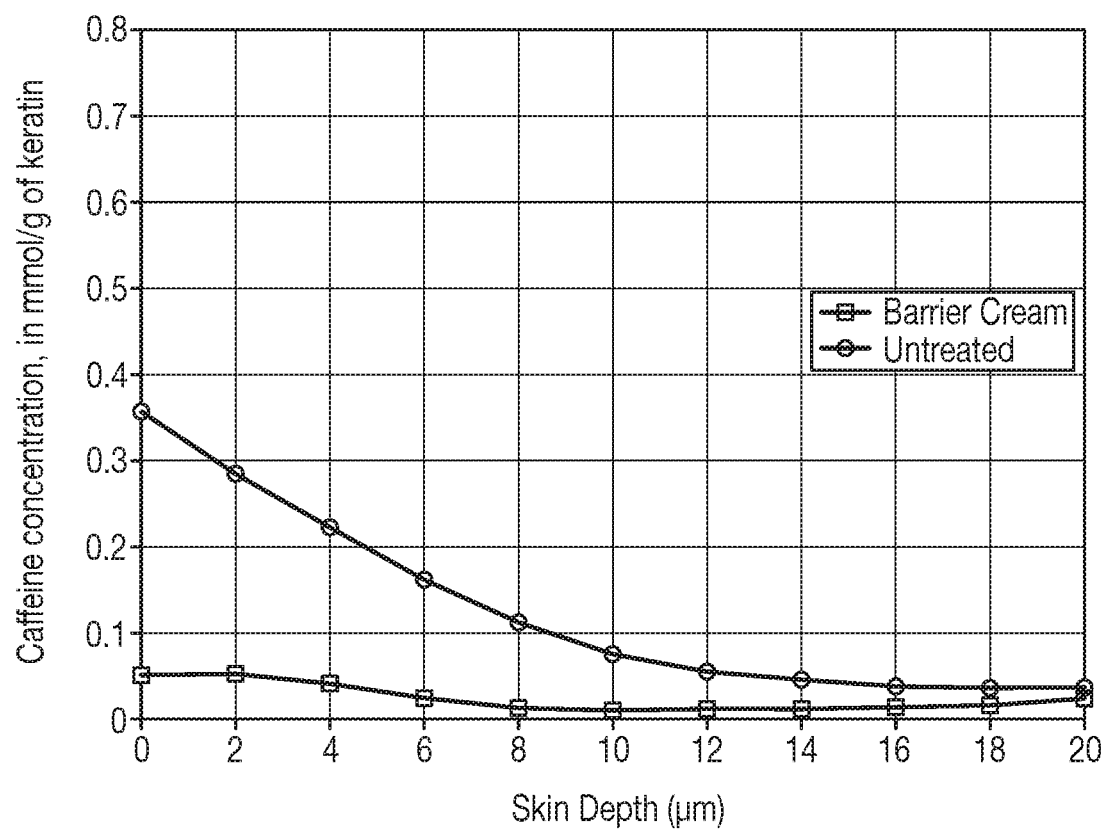
FIG. 8 shows experimental data on adult skin.

Protocol
1—5 minutes acclimatization in a temperature- and humidity-controlled room
2—Application of the topical substance on the forearm
3—30 minutes acclimatization in a temperature- and humidity-controlled room
4—Application of the caffeine patch on forearm (same location) for 30 minutes
5—Measurement in the Raman fingerprint region Results
1—Experimental Data on Adult Skin. See FIG. 8.
Data from Desitin-treated skins (Square) are compared to data from reference (Circle) untreated skins (i.e., no topical substance applied in step 2 of the protocol).

Figure 9:
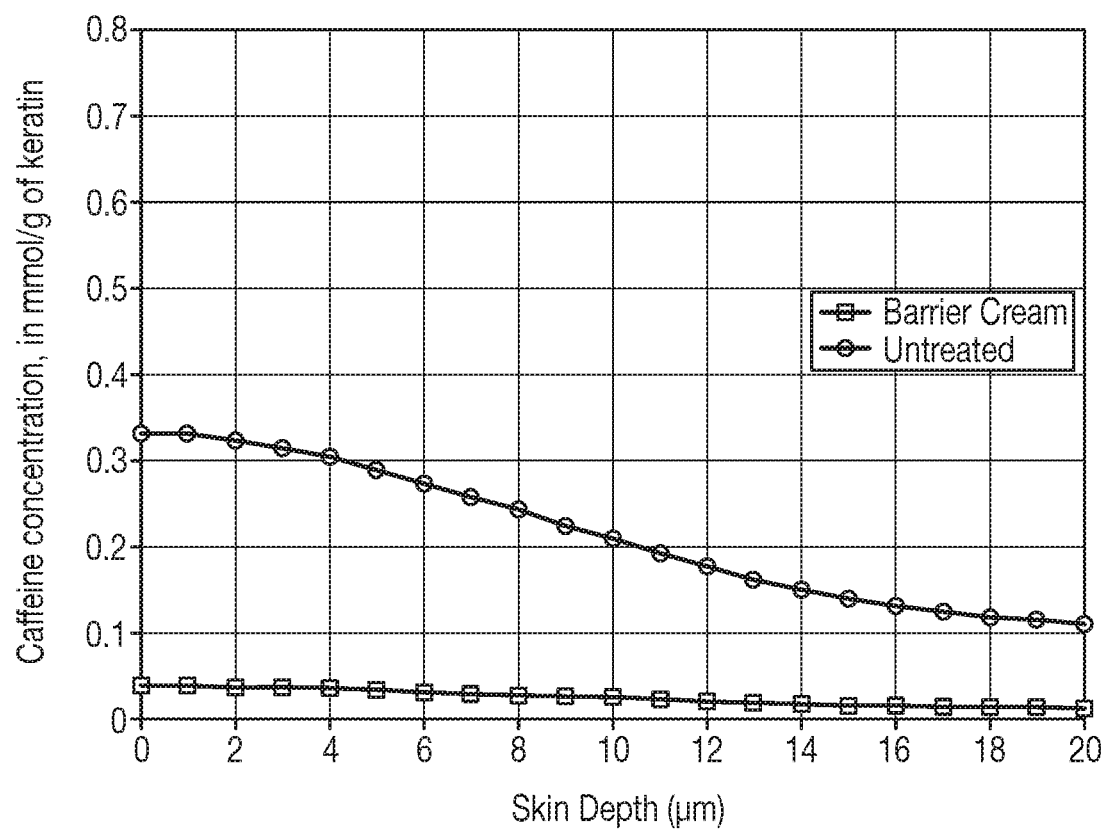
FIG. 9 shows modelization adult skin.

Penetration data are extracted from the experimental results and transferred in computational model of adult skin.
2—Modelization Adult Skin. See FIG. 9.

The next step is to define the skin permeation parameters on the computational model of the adult skin so that it can accurately simulate the experimental data presented above.

These parameters are calculated from the slope of the caffeine penetration profile.

The results from the adult model is shown below.
Barrier cream treated skin (Square) is compared to a reference untreated skin (Circle).

Figure 10:
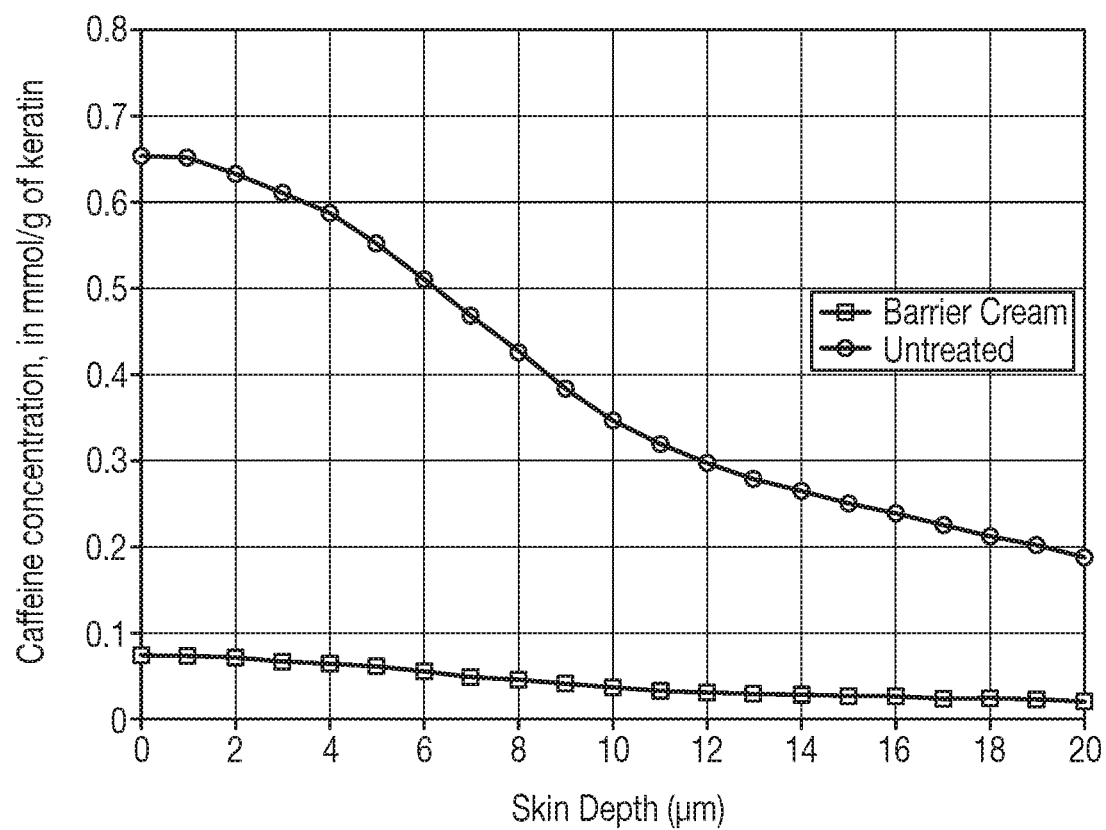
FIG. 10 shows predictive results on infant skin.

Penetration parameters are extracted from the computational adult model.
3—Predictive Results on Infant Skin. See. FIG. 10.

The last step comprises of transferring the caffeine penetration parameters with appropriate transformations to the infant skin computational model to simulate the predicted caffeine penetration in the infant skin.

Predictive results for caffeine penetration on a barrier cream treated skin (Square) and a reference untreated skin (Circle) are shown in FIG. 10.

Finally, from the ratio shown below involving the area under the curve (AUC) for the Untreated skin by the AUC for the Barrier cream-treated skin we can calculate the predicted % protection of the barrier cream:

$$\% \text{ Protection}=100\times(\text{AUC(Untreated)}-\text{AUC(Product)})/\text{AUC (Untreated)}=89.18\%$$

Examples 5 Moisturizer Simulation

Experimental data were collected on 6 volunteers, aged between 18 and 40 years.

Figure 11:
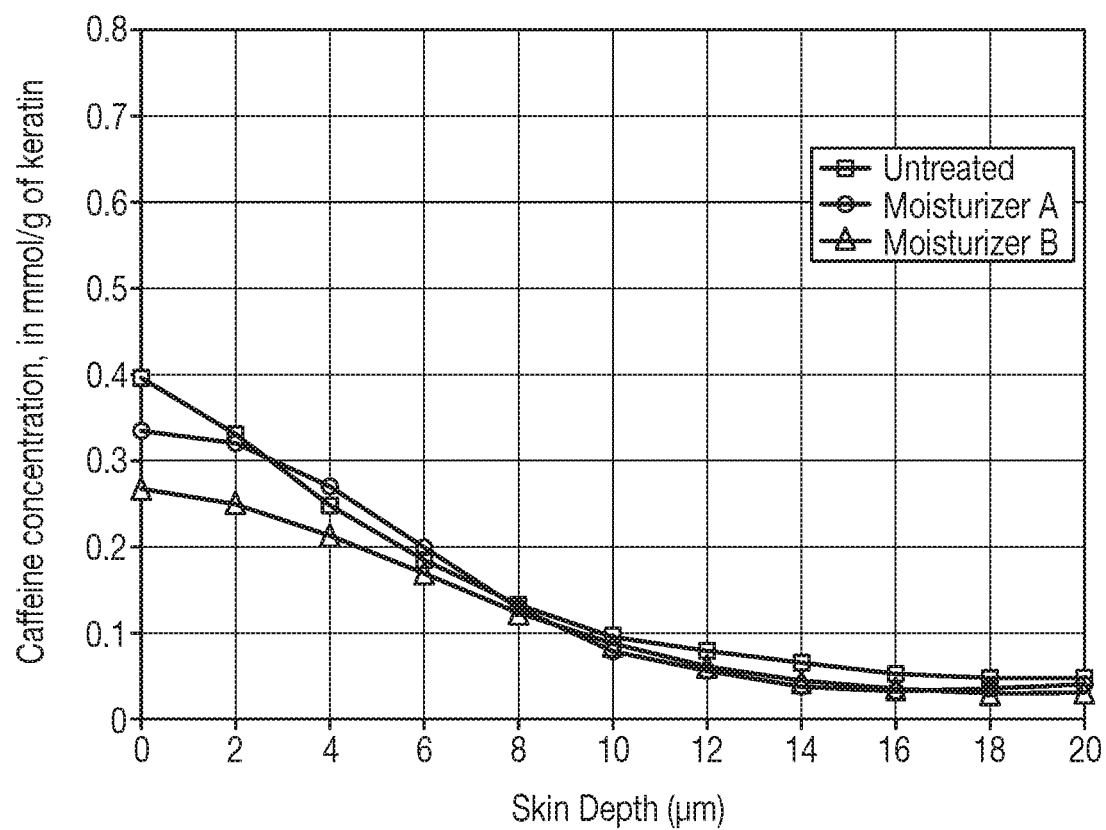
FIG. 11 shows experimental data on adult skin.

Topical substance tested:
Moisturizer A: Emulsion comprising: Glycerin (12%), Petrolatum (4%), Distearyldimonium Chloride, Water
Moisturizer B: Structured emulsion comprising: Petrolatum (40%), Glycerin (12%), Distearyldimonium Chloride, Water Protocol
1—5 minutes acclimatization in temperature/humidity-controlled room
2—Application of the topical substance on forearm for 30 minutes
3—Application of the caffeine patch on forearm (same location) for 30 minutes
4—Measurement in the fingerprint region Results
1—Experimental Data on Adult Skin
Referring to FIG. 11, data from Moisturizer A treated skins (Square) are compared to data from Moisturizer B treated skins (Triangle) and reference untreated skins (Circle) (i.e. no topical substance applied in step 2 of the protocol).

Penetration data are extracted from the experimental results and transferred in computational model of adult skin.

Figure 12:
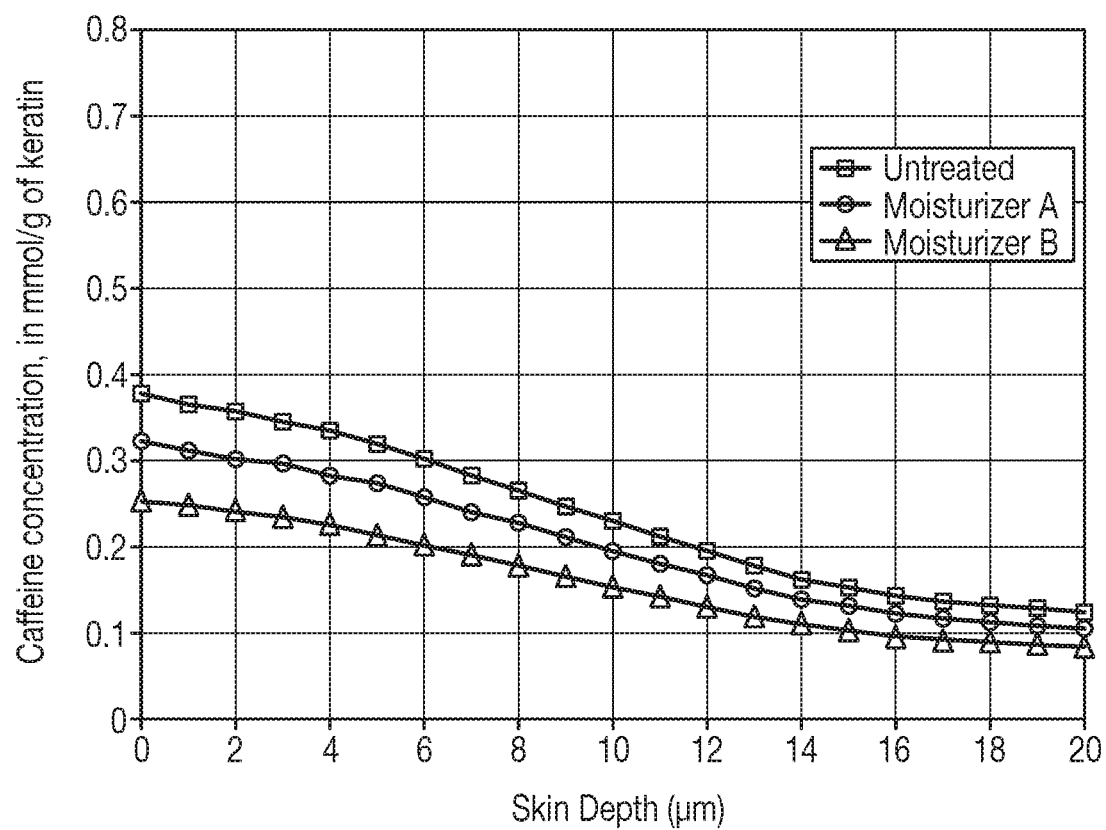
FIG. 12 shows modelization on adult skin.

2—Modelization Adult Skin. See. FIG. 12.

The next step is to define the skin permeation parameters on the computational model of the adult skin so that it can accurately simulate the experimental data presented above.

These parameters are calculated from the slope of the caffeine penetration profile. The results from the adult model is shown below.

Moisturizer A treated skin (Square) is compared to Moisturizer B treated skin (Triangle) and to a reference untreated skin (Circle).

Penetration parameters are extracted from the computational adult model.

3—Predictive Results on Infant Skin

The last step comprises of transferring the caffeine penetration parameters with appropriate transformations to the infant skin computational model to simulate the predicted caffeine penetration in the infant skin.

Figure 13:
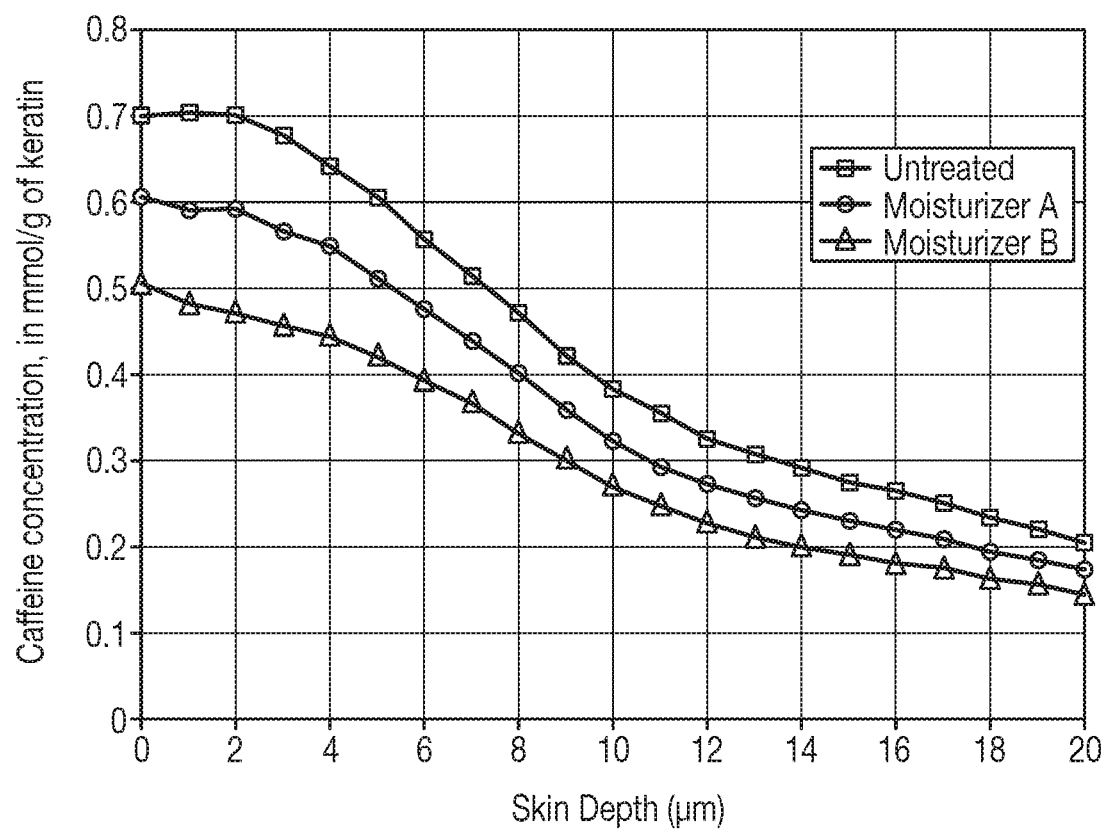
FIG. 13 shows predictive results on infant skin.

Predictive results for caffeine penetration on a Moisturizer A treated skin (Square), a Moisturizer B treated skin (Triangle) and a reference untreated skin (Circle) are shown in FIG. 13.

Finally, from the ratio shown in FIG. 13 involving the area under the curve (AUC) for the Untreated skin by the AUC for the moisturizer-treated skin we can calculate the predicted % protection of the moisturizer:

For Moisturizer A

% Protection: Not applicable

The area under the curve for moisturizer A is superior to the area under the curve for the untreated reference. The simulation predicts no protecting effect on infant skin.

For Moisturizer B

% Protection=100×(AUC(Untreated)−AUC(Product))/AUC (Untreated)=17,72%.

It will be understood that, while various aspects of the present disclosure have been illustrated and described by way of example, the invention claimed herein is not limited thereto, but may be otherwise variously embodied according to the scope of the claims presented in this and/or any derivative patent application.

The invention claimed is:

1. A method of evaluating a potential impact of a surfactant system on infant skin, comprising:
   a) topically applying said surfactant system in a non-invasive method to adult intact skin
   b) topically applying a marker to said surfactant system treated adult skin;
   c) applying confocal analysis to measure penetration of said marker into said surfactant system treated adult skin;
   d) applying a computational model of adult skin penetration to visualize penetration of the marker by optimizing penetration parameters so that the model of adult skin penetration profiles match the experimental data;
   e) transferring the optimized penetration parameters to a computational model of infant skin; and
   f) determining the penetration of the marker in the computational model of infant skin.

2. The method of claim 1, wherein the marker is caffeine.

3. The method of claim 1, wherein the EPISIM platform is employed as the computational model of adult skin penetration.

4. The method of claim 1, wherein the computational model of adult skin penetration is an agent-based model.

5. The method of claim 1, wherein the penetration parameters to be optimized are selected from the group consisting of local surface concentration and permeability coefficient.

6. The method of claim 1, wherein the marker has a traceable signal.

7. The method of claim 6, wherein the traceable signal is traceable using confocal analysis.

8. The method of claim 7, wherein the confocal analysis is selected from confocal Raman micro-spectrometry and confocal fluorescence microscopy.

* * * * *